United States Patent [19]

Watanabe

[11] Patent Number: 5,073,952
[45] Date of Patent: Dec. 17, 1991

[54] PATTERN RECOGNITION DEVICE

[75] Inventor: Masaharu Watanabe, Kanagawa, Japan

[73] Assignee: Sigmax Kabushiki Kaisha, Yokohama, Japan

[21] Appl. No.: 241,177

[22] Filed: Sep. 7, 1988

[51] Int. Cl.$^5$ .................................................. G06K 9/60
[52] U.S. Cl. ............................................ 382/8; 382/33; 358/106
[58] Field of Search ........................ 382/8, 34, 30, 33; 358/106

[56] References Cited

U.S. PATENT DOCUMENTS

| | | | |
|---|---|---|---|
| 3,781,801 | 12/1973 | Anderegg | 382/34 |
| 4,345,312 | 8/1982 | Yasuye et al. | 382/34 |
| 4,776,023 | 11/1988 | Hamada et al. | 382/8 |
| 4,803,734 | 2/1989 | Onishi et al. | 382/8 |

Primary Examiner—Michael Razavi
Assistant Examiner—Yon Jung
Attorney, Agent, or Firm—Sughrue, Mion, Zinn, Macpeak and Seas

[57] ABSTRACT

Data which represents a border line of a region of a video image to be observed and which contains a large luminance difference compared with that of a defect to be detected is excluded in judgement when it belongs to a predetermined region so that it is possible to detect a minute defect or defects reliably even when a position of a workpiece is displaced from that of a master or when the border line of the workpiece is not coincident with that of the master due to a difference in size therebetween.

4 Claims, 6 Drawing Sheets

PATTERN RECOGNITION DEVICE

BACKGROUND OF THE INVENTION

The present invention relates to a pattern recognition device and, particularly, to such device useful in recognizing minute defects on a printed circuit board, a coating of an automobile or a lens, etc., by means of a television camera.

A proposal is disclosed in Japanese Patent Application Laid-open No. 39581/1985, in which an existence of an article or defects in various portions thereof is recognized by deciding whether or not a signal level of a portion of a video signal of the article which corresponds to an area of the article to be monitored is within a predetermined range. In detail, luminance of the video signal corresponding to the monitor region of the article is compared with luminance of a video signal of a corresponding region of a standard article ( referred to as "master" hereinafter ) having a normal contour and it is decided that the monitor region contains a defect when there is a difference in luminance therebetween.

In a case where a minute defect or defects existing in a wide monitor region of a device such as a printed circuit board, an automobile coating, a lens, etc., are to be detected, it is necessary to reliably detect even a very small variation of luminance of the video signal thereof which is not included in the signal from the master Since an area of such a defect may be considerably smaller than that of the monitor region, it is difficult, practically, to derive a video signal portion corresponding to the defect from a video signal of the monitor region when there is a portion or portions, such as a curved, angled or patterned portion which may reflect illumination light considerably locally causing a wide and considerable variation of luminance to be produced regardless of defect, included in the monitor region, which may constitute a background noise large enough to make the intended video signal portion inseparable therefrom. This fact is very severe when the portion in question is a border line of the monitor region.

When the latter is the case and when the video signal of the monitor region is displaced in position relatively to that of the master or the monitor region is different in size from the master region, luminance information obtained from such displaced border region becomes considerably larger than that of the minute defect even if such positional displacement is within an acceptable range and thus it becomes impossible to distinguish the defect therefrom.

Therefore, in order to detect such a minute defect precisely, it is necessary to successively compare respective pixels of the monitor region with those of the master region one by one. In this case, the problem of the positional displacement between the monitor and the master regions becomes very severe causing this approach not to be practical.

SUMMARY OF THE INVENTION

An object of the present invention is to provide a pattern recognition device capable of detecting a minute defect included in a wide region without influence of portions in the wide region in which large difference in luminance is included.

According to the present invention, the above object of the present invention is achieved by a provision of a pattern recognition device in which, in comparing first video image data obtained by a TV camera from monitor region with a second video image data obtained by the TV camera from a master, image data portions concerning border areas of the monitor regions are excluded.

BRIEF DESCRIPTION OF THE DRAWING

FIG. 5 which is comprised of FIGS. 5A and 5B is a block circuit diagram showing an embodiment of the present pattern recognition device; and FIG. 6 which is comprised of FIGS. 6A and 6B is a flow-chart showing an operation of the present pattern recognition device.

DETAILED DESCRIPTION OF THE PREFERRED EMBODIMENT

Figure 1:
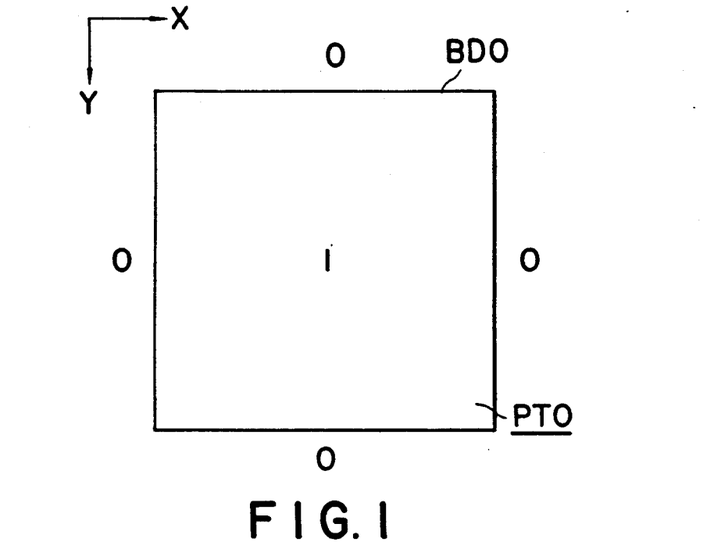
FIGS. 1 to 4 illustrate a principle of the present pattern recognition device.

Before describing an embodiment of the present invention, it may be helpful in fully understanding the present invention to describe a principle of the present invention. FIGS. 1 to 4 illustrate the principle, in which FIG. 1 shows an original image PT0 having an area defined by a border BD0. Luminance of the original image PT0 is assumed as 1 and an outside area of the image is indicated as having luminance 0.

Figure 2:
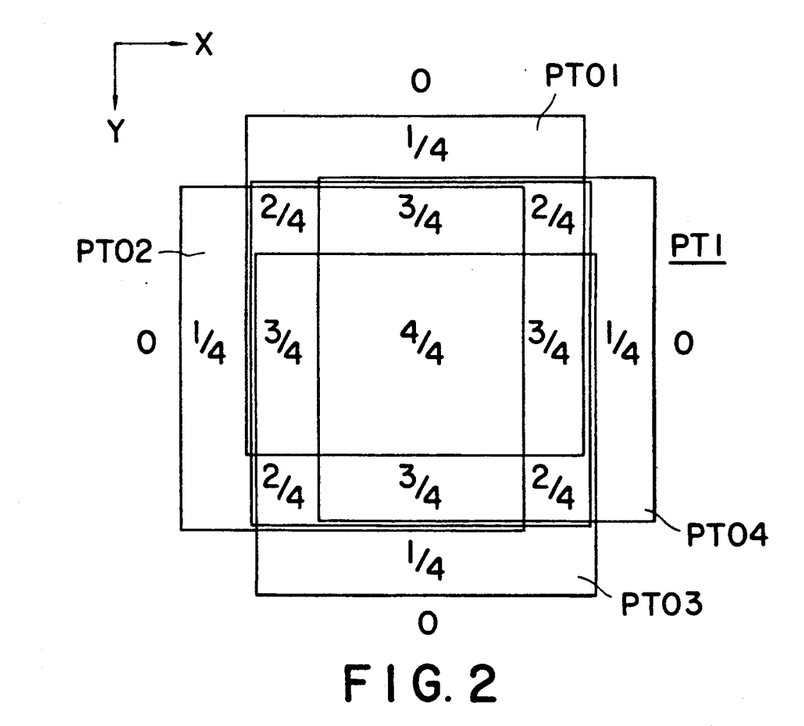

FIG. 2 shows shift images PT01 and PT03 obtained by shifting the original image PT0 in FIG. 1 vertically up and down by one pixel, respectively, and PT02 and PT04 obtained by shifting the original image PT0 horizontally left and right by one pixel, respectively. Luminance information of a desired number (in this case, four) of such shifted images are overlapped as shown in FIG. 2 and a sum of luminance information for each pixel area is obtained. An average luminance of an overlapped image PT1 is obtained according to the following equation:

$$PT1 = (PT01 + PT02 + PT03 + PT04)/4 \tag{1}$$

Figure 3:
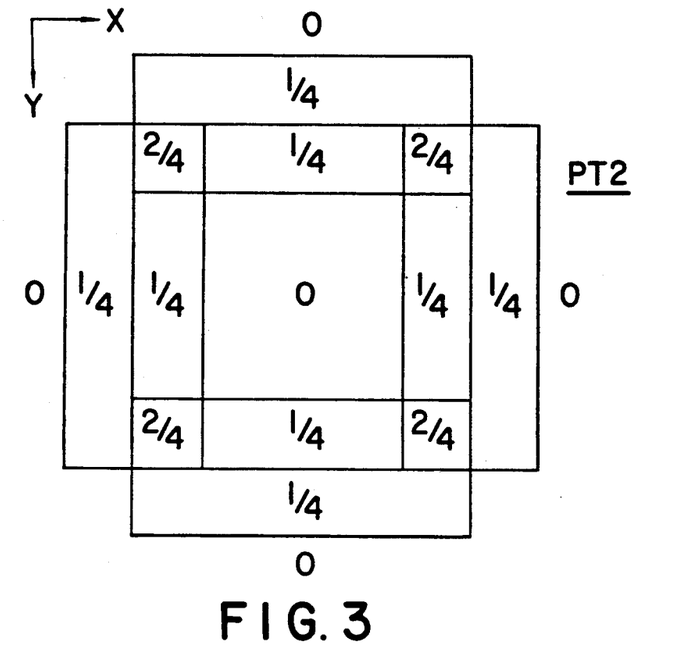

Then, the luminance information of the overlapped image PT1 is reduced by the original image PT0 and an absolute value of a resultant difference, which is given below, is assigned to each of the pixels constituting the respective image portions, resulting in a difference image PT2 as shown in FIG. 3.

$$PT2 = |PT0 - PT1| \tag{2}$$

Thus, only the border information added by the overlapping processing shown in FIG. 2 is left as it is.

Figure 4:
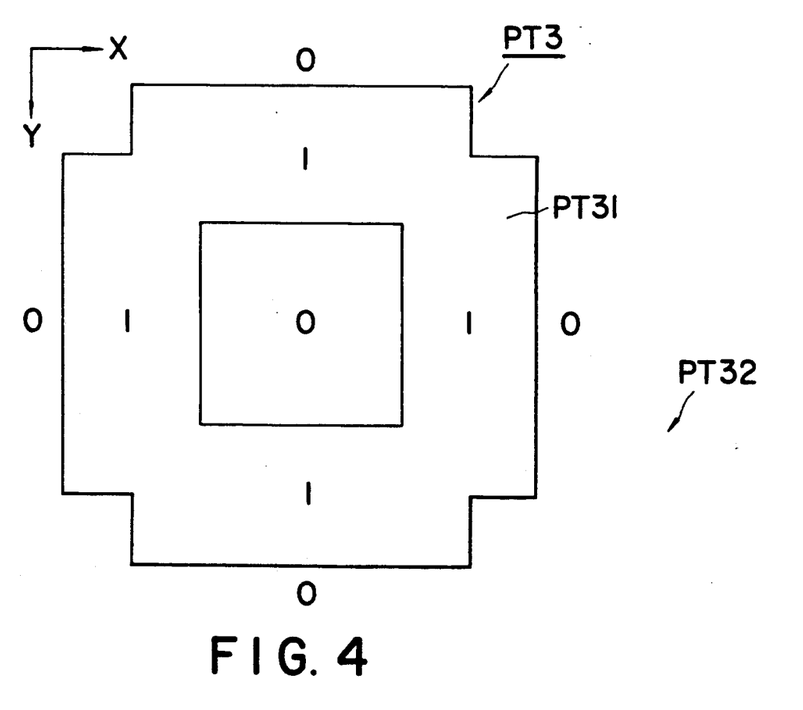

Thereafter, a threshold level of luminance is set to a predetermined value TH according to the luminance information of the difference image PT2 in such a manner as shown below $$TH = \frac{1}{4} \tag{3}$$

and, then, pixels of the difference image PT2 which have luminance equal to or higher than the set level are assigned to a logic level "1" when $$PT2 \geq TH \tag{4}$$

as shown by $$PT3 = \text{"1"} \tag{5}$$

and to a logic level "0" when $$PT2 < TH \tag{6}$$

as shown by $$PT3 = "0" \tag{7}$$

to define a boundary excluded image PT3 as shown in FIG. 4. That is, a boundary excluded area PT31 of the boundary excluded image PT3 to which logic level "1" is assigned is excluded and a comparison with the master is performed only for an area PT32 to which logic level "0" is assigned.

Therefore, so long as a sample to be monitored on defect is located such that its border area falls in the area PT31, a defect of similar size to one pixel existing in the area PT32 can be reliably detected by the comparison with the master having no such defect.

The operation of the equation (1) can be represented generally as follows:

$$\overline{f(X,Y)} = \frac{\sum_{j=-m}^{m}\sum_{i=-n}^{n} f(X + \Delta X, Y + \Delta Y)}{(2m + 1) \cdot (2n + 1)} \tag{8}$$

where $\Delta X$ and $\Delta Y$ are shift amount data in X and Y directions and represented by $$\Delta X = i \cdot \Delta_x (i = -n \sim +n) \tag{9}$$

and $$\Delta Y = j \cdot \Delta_y (j = -m \sim +m) \tag{10}$$

where $\Delta_x$ and $\Delta_y$ are unit shifts of an image in X and Y directions and $$\overline{f(X,Y)}$$

represents an integration of a luminance f(X,Y) at a position (X,Y) on the image plane. Thus, it is possible to obtain mean luminance of pixels constituting the respective image portions by overlapping (2m+1) (2n+1) shifted images. It should be noted that the operation of the equation (8) is equivalent to obtain a smoothed image by filtering the original image PT0 (FIG. 1) through a spatial low-pass filter.

The comparison of the threshold level TH with the luminance of the difference image PT2 can be represented as follows:

$$|f(X,Y) - \overline{f(X,Y)}| \geq TH \tag{11}$$

$$|f(X,Y) - \overline{f(X,Y)}| < TH \tag{12}$$

Figure 5A:
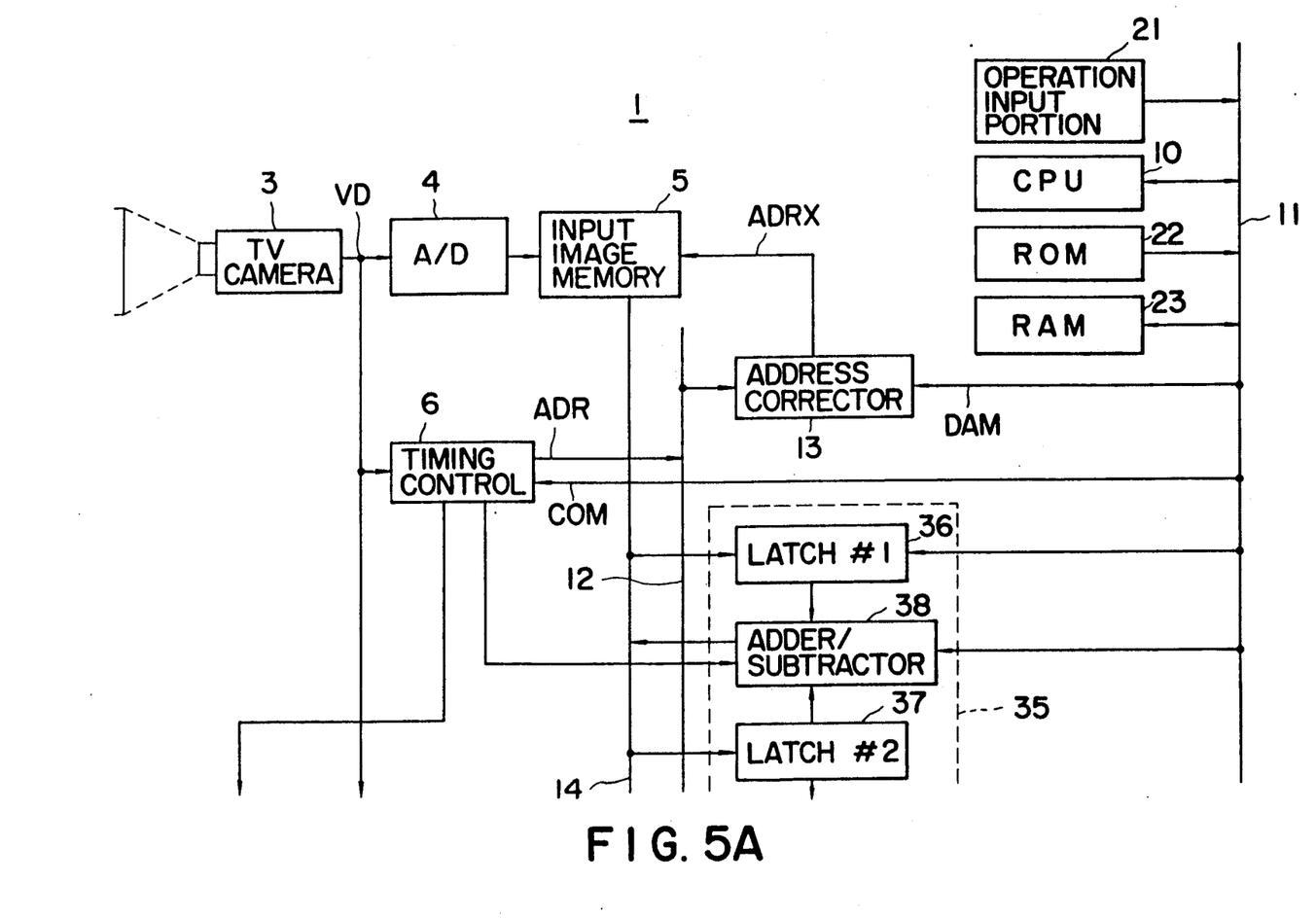
Figure 5B:
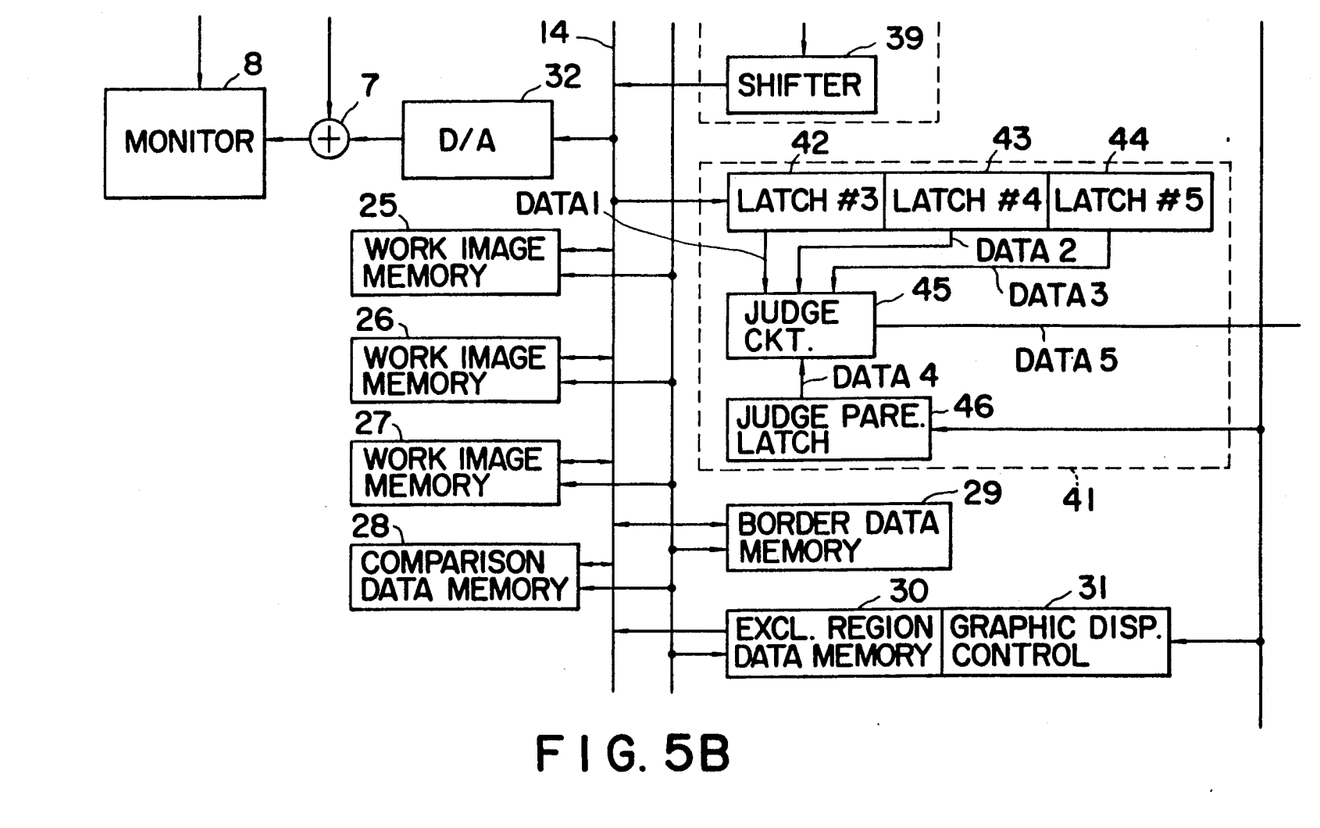

FIG. 5 shows, in block diagram, a general construction of an embodiment of the pattern recognition device according to the present invention. In FIG. 5, a video image signal VD of a workpiece 2 such as a lens to be checked for defects is obtained by a TV camera 3, which is converted by an A/D converter 4 into a digital data signal of a predetermined number of bits, e.g., 8 bits. The digital data is stored in an input image memory 5 comprising a frame memory.

The video signal VD is also directly supplied to a timing control circuit 6 and is supplied to a monitor 8 through a superimpose circuit 7.

The timing control circuit 6 generates a clock signal in synchronism with horizontal and vertical synchronizing signal portions of the video signal VD, forms an address data signal ADR in response to an instruction signal COM from a CPU 10 received through a CPU bus 11 and sends it to a video address bus 12 so that address data can be sent to a plurality of image memories 25 to 27 connected to the video address bus 12 pixel by pixel.

The image signals data written in the input image memory 5 are read out sequentially according to correction address data ADRX obtained in an address correction circuit 13 on the basis of the address data ADR from the timing control portion 6 and transferred through a video data bus 14. That is, the address correction circuit 13 corrects the address data ADR according to a correction data signal $D_{AM}$ supplied from the CPU 10 by amounts corresponding to the shift amounts $\Delta X$ and $\Delta Y$ and the resultant correction address data ADRX is sent to the input image memory 5 so that image data of the shifted images PT01 to PT04 previously mentioned with respect to FIG. 2 can be sent to the video data bus 14 under the control of the CPU 10.

The CPU 10 responds to an instruction signal from an operation input portion 21 to execute, with the aid of a RAM 23, a pattern recognition processing program according to a program data stored in a ROM 22.

The working image memory 25 connected to the data bus 14 comprises a frame memory of, for example, 16 bits and functions to store luminance information of the overlap image PT1 obtained on the basis of luminance information of the original image PT0 as mentioned with reference to FIGS. 2 and 3. The working memory 25 further functions to store luminance data of the difference image PT2 obtained on the basis of the overlap image PT1 and the original image PT0 as mentioned with reference to FIG. 3 and an image data of the workpiece.

A comparison data memory 28 also connected to the data bus 14 stores a result of comparison of the image data of the workpiece with the image of the master image of the workpiece.

A boundary data memory 29 also connected to the data bus 14 stores data of the boundary excluded image PT3 obtained with respect to the master image as mentioned with reference to FIG. 4.

A boundary exclusion area data memory 30 also connected to the video data bus 14 functions to store pattern data generated by a graphic display controller 31, under control of the CPU 10. When CPU 10 controls the graphic display controller 31 according to instruction data from the operation input portion 21, the image data in the boundary exclusion area data memory 30 is displayed through a D/A converter 32 and the superimpose circuit 7 on the monitor 8 such that data of the area to be excluded in the on test, i.e., the area of the image having a large variation of luminance while not being considered as a final product, can be stored selectively in the boundary exclusion area memory 30 manually.

A data operation circuit 35 connected to the video data bus 14 executes the operations of the boundary data mentioned with respect to the equations (1) to (10).

That is, in performing the summing operation mentioned with respect to the equations (1) and (8) or the subtracting operation shown by the equations (2) and (9), data to be added or subtracted is latched in first and second latch circuits 36 and 37 and the operation is performed in an addition/subtraction circuit 38 under control of the CPU 10.

In performing the division operation of equations (1) and (8), data to be divided is put in the second latch circuit 37 and shifted by a shifter 39 toward a least significant bit.

In addition thereto, in performing the comparisons between the difference image PT2 and the threshold level TH shown by the equations (4) and (6) and the equations (9) and (10), data of the threshold level TH is written from the CPU 10 into the first latch circuit 36 and the data of the difference image PT2 in the second latch circuit 37. By subtracting one of these data from the other in the adder/subtractor circuit 38, a logical level of the boundary excluded image PT3 (FIG. 4) is judged.

A judge portion 41 is also connected to the video data bus 14. The judge portion 41 includes a third, a fourth and fifth latch circuits 42, 43 and 44. The third latch circuit 42 stores luminance data of the workpiece, the fourth latch circuit 43 stores the data of the boundary excluded image PT3 and the fifth latch circuit 44 stores data concerning the excluded area from the detection exclusion area memory 30.

Data signals DATA1, DATA2 and DATA3 stored in the respective latch circuits 42, 43 and 44 are supplied to a judge circuit 45 by which an acceptability of the workpiece is judged, together with a judge parameter data signal DATA4 set by the CPU 10 in a judge parameter latch circuit 46, a resultant data signal DATA5 of this judgement is provided as a judge output of the pattern recognition device of this embodiment.

Figure 6A:
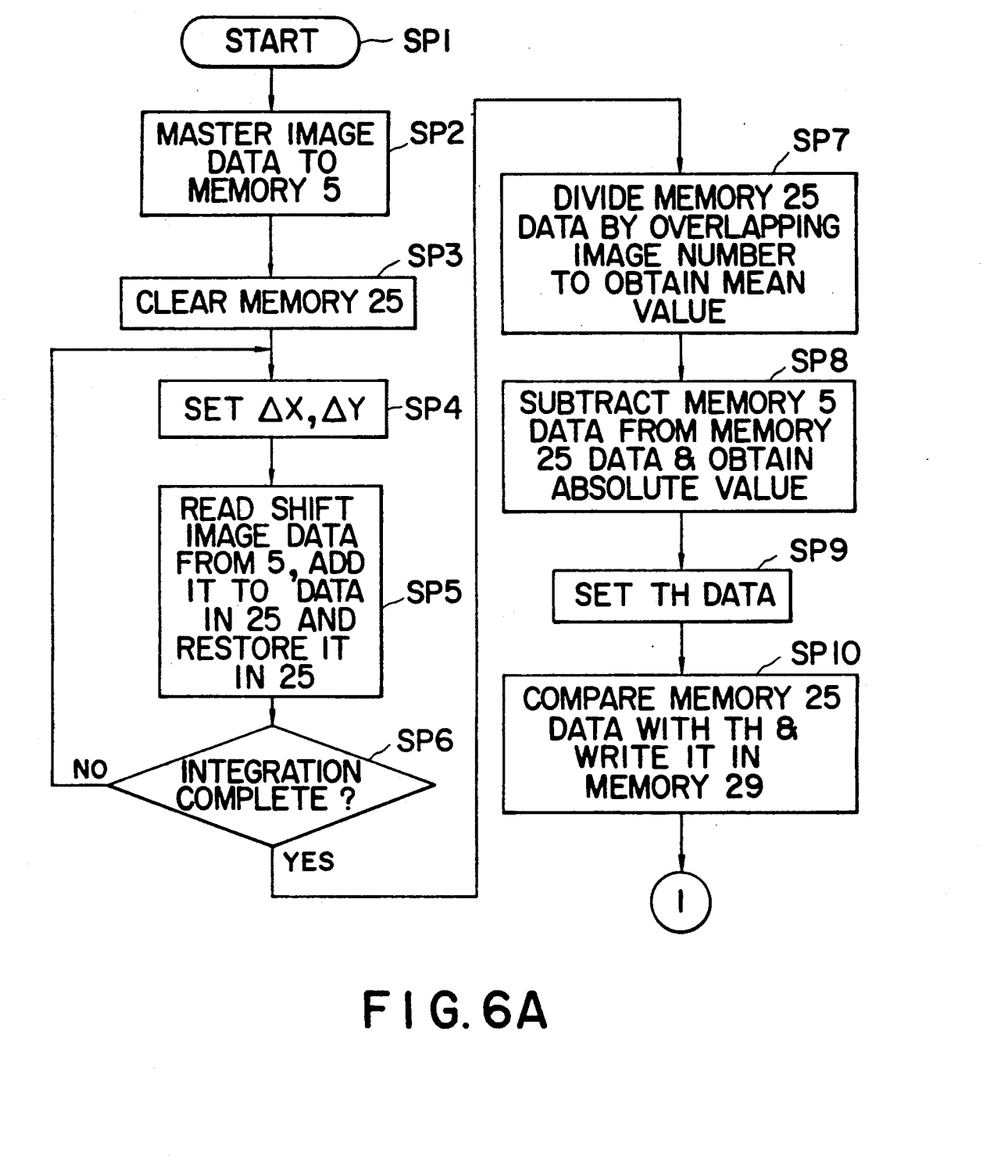
Figure 6B:
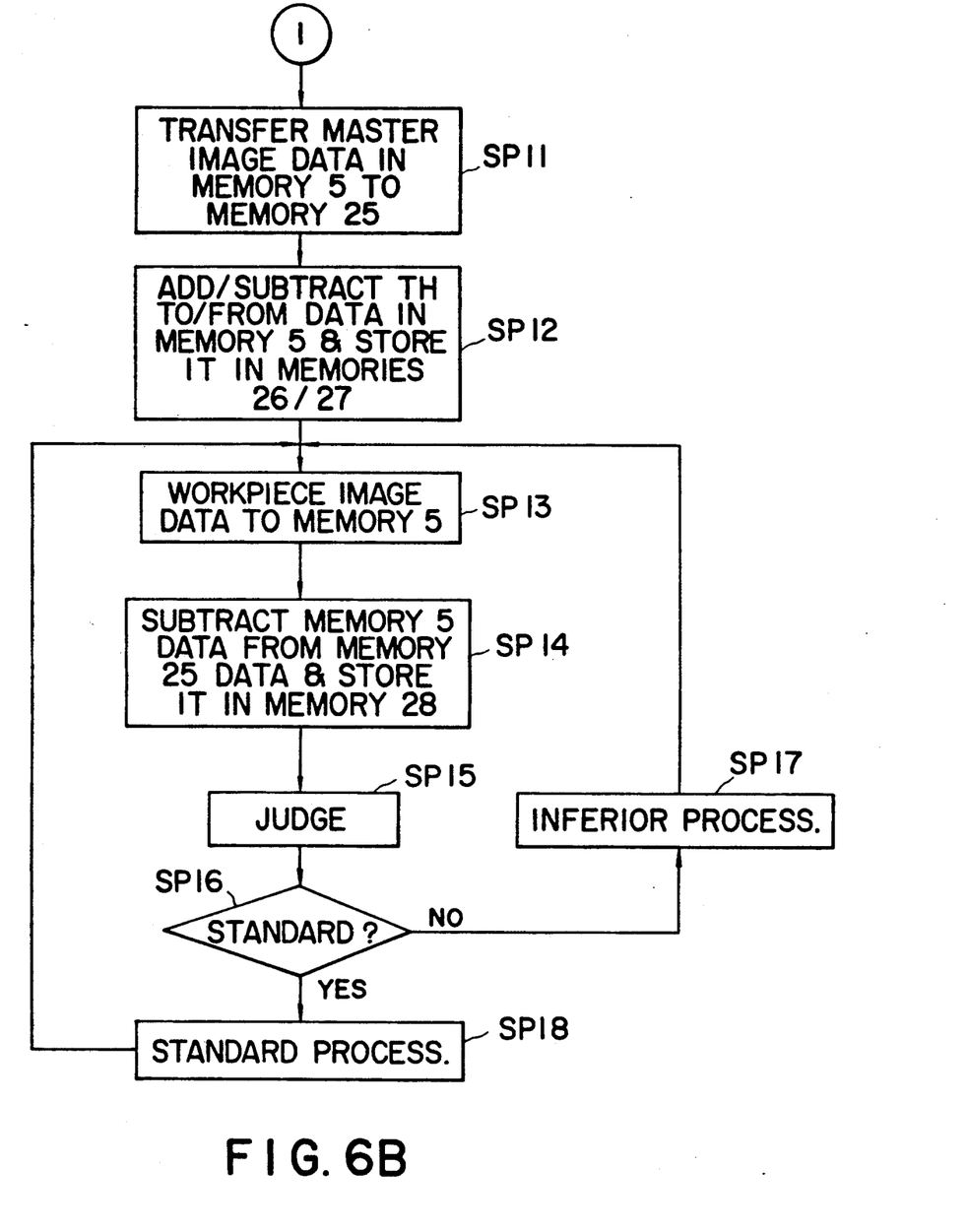

The pattern recognition device shown in FIG. 5 operates to judge whether or not the workpiece 2 has one or more minute defects according to a program shown in FIG. 6.

In FIG. 6, the CPU 10 starts to operate in the step SP1 at which the master workpiece 2 has been set with respect to the TV camera 3. In the step SP2, the CPU 10 picks up a frame of image data in the input image memory 5 on the basis of a video signal VD of the master workpiece. Simultaneously, the CPU 10 sets the address correction data $\Delta X=0$ and $\Delta Y=0$ in the address correction circuit 13, so that the address data ADR in the timing control circuit 6 is input to the input image memory 5 as the corrected address data ADRX upon which the data of the original master image PT0 (FIG. 1) is set in the input image memory 5.

Then, in the step SP3, the CPU 10 clears image data stored in the working image memory 25 and, in the step SP4, it sequentially sets the correction data $D_{AM}$ composed of the shift data $\Delta X$ and $\Delta Y$ mentioned with respect to the equations (9) and (10) in the address correction circuit 13 pixel by pixel.

Thus, in the step SP5, data of an image shifted in X and Y directions by $\Delta X$ and $\Delta Y$ at a timing of the, address data ADR from the timing control portion 6 are read out pixel by pixel and, after being added to the image data stored in the working image memory 25 in the data operation circuit 35, is rewritten in the working image memory 25.

Thereafter, in the step SP6, the CPU 10 judges whether or not the integration is completed and, if not, the operation is returned to the step SP4 to execute the operations in steps SP4 and SP5 for a next pixel. In the similar manner, the CPU 10 repeats the operations in the steps SP4, SP5, SP6 to SP4 for luminance data of respective pixels of respective shifted images $i= -n \sim +n, j= -m \sim +m$ and the integration for all of the shifted images PT1 to PT4 is completed. Thus, the integrated image data for obtaining the overlapped image PT1 mentioned with respect to FIG. 2 is stored in the working image memory 25.

Under the circumstances, the judgement in the step SP6 becomes yes and then the operation is shifted to the step SP7 in which the data in the working image memory 25 is transferred to latch circuit 37 of the operation circuit 35 and, after being divided in the shifter 39, returned to the working image memory 25. Thus, the overlapped image PT1 shown in FIG. 2 is stored in the working image memory 25.

Thereafter, the operation is shifted to the step SP8 in which the data in the working image memory 25 is read out to the latch circuit 37 of the data operation circuit 35 pixel by pixel and image data of corresponding pixels thereto are readout from the input image memory 5 to the latch circuit 36 and, after the subtraction operation shown by the equation (2), an absolute value of a result thereof is returned to the working image memory 25. Therefore, the image data of the differential image PT2 (FIG. 3) is obtained in the working image memory 25.

Then, the operation is shifted to the step SP9 in which the data of the threshold level TH is set in the latch circuit 36 and then, in the step SP10, the image data of the difference image PT2 stored in the working image memory 25 is compared with the data of the threshold level TH in the latch circuit 36 pixel by pixel and data of 1 bit corresponding to the sign of the difference thereof is written in the boundary data memory 29 which now stores the image data of the boundary excluded image PT3 (FIG. 4).

Now, the setting and processing of the image PT3 representing the detection exclusion area PT31 to be excluded in judging the boundary of the master is completed.

Thereafter, the operation is shifted to the step SP11 in which the image data in the input image memory 5 is transferred to the working image memory 25 for subsequent judgement of the acceptability of workpieces.

Then, the operation is shifted to the step SP12 in which the image data in the input image memory 5 is readout to the latch circuit 37 and subjected to an addition and a subtraction with respect to the data of the threshold level TH set therein, results being stored in the working image, memories 26 and 27 as an upper data limit and a lower data limit, respectively.

Thus, the processing of the image data of the master is completed and the operation of the CPU 10 is shifted to a processing step for judging acceptability of workpieces set with respect to the TV camera 3 one by one on the basis of the data of the master. After image data based on a video signal VD of the workpiece is stored in the input image memory 5 in the step SP13, the operation is shifted to the step SP14 in which the image data in the memory 5 is transferred to the latch circuit 36 and the image data in the working image memory 25 is transferred to the latch circuit 37. These data are subjected to a subtraction operation in the adder/subtractor circuit 38, an absolute value of a result of which is written in the comparison data memory 28.

Since the working image memory 25 stores the image data of the master and the input image memory 5 stores the image data of the workpiece to be judged, the comparison data memory 28 stores difference data in luminance between respective pixels of the master image and the workpiece image.

The difference data is also considered for the boundary regions of the master image and the workpiece image and is stored in the comparison data memory 28 as data representing a difference in video signals VD obtained from the TV camera 3. Therefore, when a position of the workpiece is displaced from the position of the master, the luminance difference becomes large since the boundary regions thereof are displaced from each other. When a size of the workpiece is different from that of the master, it is stored in the comparison data memory 28 as data representing a large luminance difference since the boundary regions thereof are displaced largely from each other.

Such difference data of the boundary region is excluded in judging the acceptability of the workpiece in the step SP15.

That is, in the step SP15, the data of the threshold level TH is latched in the latch circuit 36 and the image data in the comparison data memory 28 is latched in the latch circuit 37 pixel by pixel. These latched data are compared in the adder/subtractor circuit 38 and a comparison data of one bit represented by a sign of an output of the circuit 38 is latched in a third latch circuit 42 of the judge operation portion 41.

At the same time, the CPU 10 latches the data of the boundary excluded image PT3 in the boundary data memory 29 in a fourth latch circuit 43 and latches the data in the detection exclusion area data memory 30 in a fifth latch circuit 44.

Thus, the judge circuit 45 responds to the data DATA1, DATA2 and DATA3 from the latch circuits 42, 43 and 44 to provide a judge data DG which is logical 1 when DATA1=1, ∩DATA2=0 and ∩DATA3=0, that is, when luminance of a pixel of the workpiece is the same as that of the master, the pixel is included in the detection region PT32 (FIG. 4) and the pixel is not included in the detection exclusion region PT31, and logical 0 when DATA1=0, ∪DATA2=1 or ∪DATA3=1, that is, when luminance of the pixel of the workpiece is different from that of the master, the pixel does not belong to the detection region PT32 or the pixel belongs to the detection exclusion region PT31.

The judge circuit 45 counts the number of pixels for which the judge data DG obtained is logical "1" and the CPU 10 provides a judgement data signal DATA5 indicative of a negative decision in the step SP16 when the number of the pixels is larger than the value indicated by the data signal DATA4 set in a judge parameter latch circuit 46 by the CPU 10. Then, the operation is shifted to the step SP17 in which processing for a defective workpiece is performed and, then, returned to the step SP13.

When the counted pixel number is smaller than the content of the data signal DATA4, the CPU 10 provides the data signal DATA5 indicative of a positive decision and the operation is shifted to the step SP18 in which processing for an acceptable workpiece is performed and, then, returned to the step SP13.

According to the embodiment mentioned above, the data which represents the border line of the region to be observed and which contains large luminance difference compared with that to be detected is excluded in judgement when it belongs to the predetermined region PT31 (FIG. 4). Therefore, it is possible to detect one or more minute defects reliably even when the position of the workpiece is displaced from that of the master or the border line of the workpiece is not coincident with that of the master due to a difference in size therebetween.

In another embodiment of the present invention, the equation (8) is replaced by the following equation.

$$\overline{f(x,y)} = \frac{\sum_{j=-m, j\neq 0}^{m} \sum_{i=-n, i\neq 0}^{n} f(x + i \cdot \Delta_x, y + j \cdot \Delta_y)}{2m \cdot 2n} \quad (13)$$

That is, although, in the equation (8), the case where $i=0$ and $j=0$ is considered to obtain the mean luminance of each pixel, the case is excluded in the equation (13).

What is claimed is:

1. A defect recognition device for a video image region of a workpiece, comprising:
   means for obtaining first video image data corresponding to said video image region of said workpiece;
   means for obtaining second video image data of a master which corresponds to said video image region;
   means for comparing said first video image data with said second video image data, including:
   means for shifting an original video image represented by the second video image data in predetermined directions by a predetermined distance to produce a plurality of shifted images,
   means for forming overlap image data representing an overlap image formed by overlapping said original image with said shifted images, and
   means for forming difference image data by computing the difference between said overlap image data and said original image data;
   means for excluding from the output of said comparing means image data portions of said first and said second video image data corresponding to border regions of said first and second video image data, said excluding means comprising means for producing image data including data corresponding to a region to be excluded and a region to be observed by comparing said difference image data with a predetermined threshold value, said excluding means excluding portions of said first and second image data corresponding to said data of said region to be excluded from an output of said producing means; and
   judging means responsive to an output of said excluding means for judging whether said workpiece includes one or more defects.

2. The defect recognition device as claimed in claim 1, wherein said border regions between said video image monitor region and said region outside of said video image monitor region correspond to edges of said workpiece.

3. The defect recognition device as claimed in claim 1, wherein said judging means judges a coincidence of said first video image data with said second video image data when luminances of respective pixels of said first and said second video image data are equal to each other and said pixels are not within said region to be excluded but are within said region to be observed.

4. The defect recognition device as claimed in claim 3, wherein said border regions between said video image monitor region and said region outside of said video image monitor region correspond to edges of said workpiece.

* * * * *